(12) United States Patent
Espinal

(10) Patent No.: US 11,167,076 B1
(45) Date of Patent: Nov. 9, 2021

(54) MEDICAL DEVICE THAT PREVENTS AIR LEAKAGE AND ENVIRONMENTAL CONTAMINATION DURING TUBE REMOVAL FROM PATIENT

(71) Applicant: EHK MEDICAL, LLC, Akron, OH (US)

(72) Inventor: Eric A. Espinal, Akron, OH (US)

(73) Assignee: EHK Medical, LLC, Akron, OH (US)

( * ) Notice: Subject to any disclaimer, the term of this patent is extended or adjusted under 35 U.S.C. 154(b) by 0 days.

(21) Appl. No.: 16/888,107

(22) Filed: May 29, 2020

(51) Int. Cl.
*A61F 13/02* (2006.01)
*A61M 1/00* (2006.01)

(52) U.S. Cl.
CPC .......... *A61M 1/964* (2021.05); *A61F 13/0216* (2013.01); *A61F 13/0246* (2013.01); *A61M 1/743* (2021.05); *A61M 1/782* (2021.05)

(58) Field of Classification Search
CPC .......... A61M 25/02; A61M 2025/0266; A61M 2025/0273; A61M 2025/028; A61M 1/0092; A61M 1/0035; A61M 1/005; A61F 13/0246; A61F 13/0216
See application file for complete search history.

(56) References Cited

U.S. PATENT DOCUMENTS

| | | | | |
|---|---|---|---|---|
| 5,569,207 A | * | 10/1996 | Gisselberg | A61M 25/02 604/175 |
| 6,386,872 B1 | * | 5/2002 | Mukasa | A61C 5/64 206/219 |
| 6,569,121 B1 | * | 5/2003 | Purow | A61M 27/00 128/898 |
| 7,244,245 B2 | | 7/2007 | Purow et al. | |
| 7,338,482 B2 | * | 3/2008 | Lockwood | A61M 1/0084 601/6 |
| 2011/0106030 A1 | * | 5/2011 | Scholz | A61M 1/0088 604/319 |
| 2018/0318477 A1 | * | 11/2018 | Eksteen | A61F 13/00068 |

* cited by examiner

*Primary Examiner* — Nathan R Price
*Assistant Examiner* — Courtney B Fredrickson
(74) *Attorney, Agent, or Firm* — Fay Sharpe LLP

(57) ABSTRACT

A medical device for use with an associated tube inserted into an incision formed in skin or tissue of a patient includes a dressing including an opening sized to receive and allow movement of the associated tube. A valve is operatively connected with the opening of the dressing and includes a main body; and an opening formed in a portion of the main body. The opening is sized and dimensioned to accommodate the surgical tube.

19 Claims, 14 Drawing Sheets

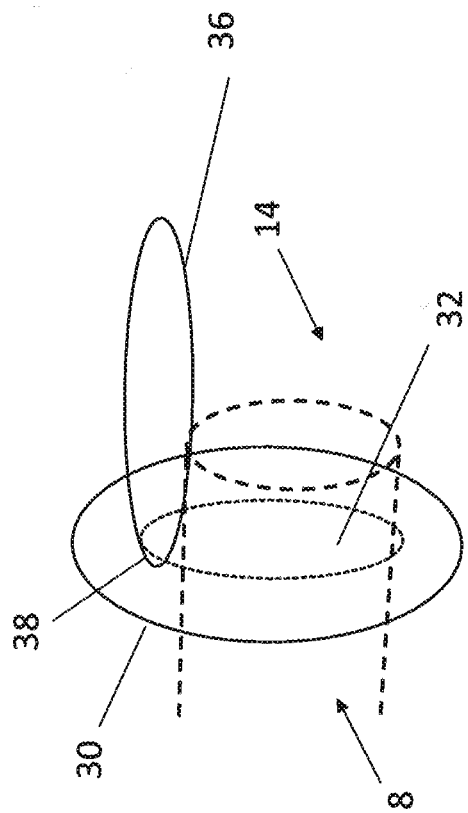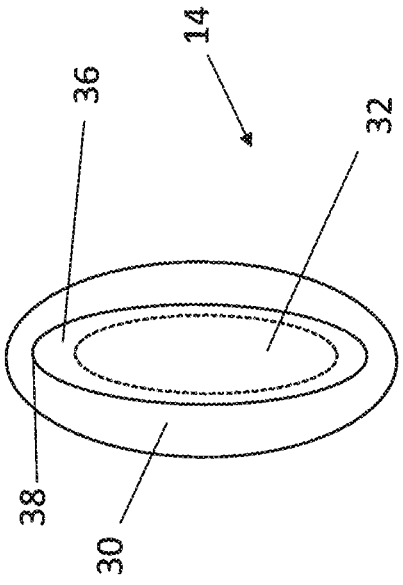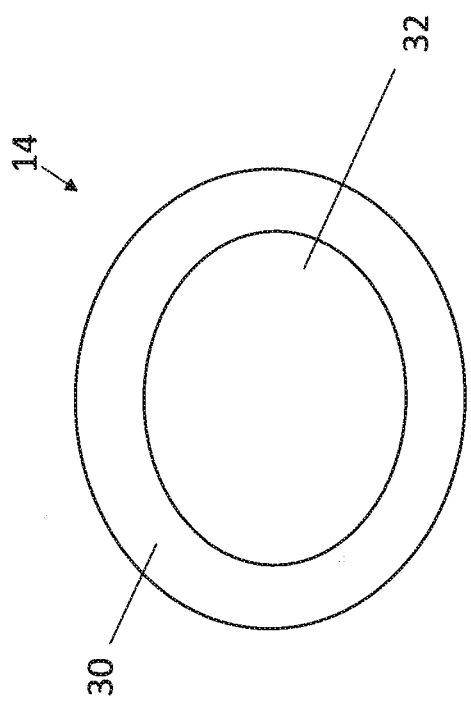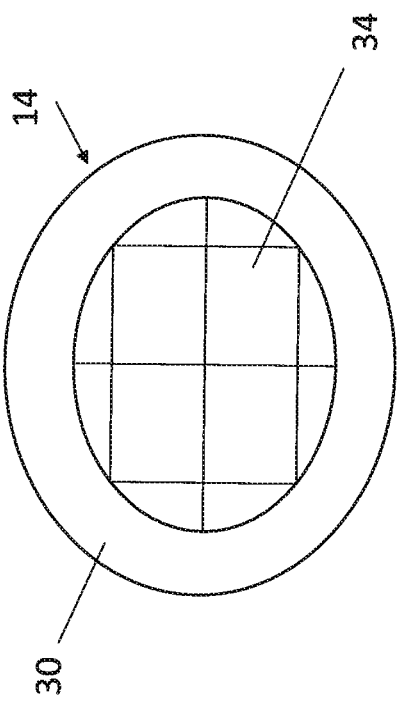

MEDICAL DEVICE THAT PREVENTS AIR LEAKAGE AND ENVIRONMENTAL CONTAMINATION DURING TUBE REMOVAL FROM PATIENT

BACKGROUND

This disclosure relates to a device or apparatus for sealing an incision of a patient, and using the device or apparatus to allow for safe, sanitary removal of a surgical tube from the incision. For example, this disclosure describes exemplary embodiments for a valve installed on a dressing to allow sealing of an incision and accommodate a tube inserted into a patient, and a sheath configured to surround the tube for a safe, sanitary removal of the tube from the patient. However, it will be appreciated that the disclosed concepts may have usefulness in manipulation of other implantable medical devices, such as various types of leads, intravenous lines, cannulas, feeding tubes, endotracheal tubes, and other therapy delivery tubes.

By way of background, the pleural chest cavity of a patient is normally a fluid-tight and air-tight environment. However, fluid or air may enter the pleural chest cavity due to disease or injury, and would need to be drained. To do so, an incision is typically formed in the chest of the patient, and a chest tube is inserted through the incision to the pleural chest cavity of a patient to drain the fluid and/or air. The chest tube can normally include draining holes, and can lead to a collection component (e.g., a pleural evacuation system, a bag, a jar, a container, and so forth) to collect the drained fluid. Once the fluid or air substance is drained, the tube is removed from the pleural chest cavity via the incision, and the incision is either sutured, or an air-tight dressing is applied.

However, a dressing alone may not fully seal the incision and result in leakage of air through the incision into the pleural space, resulting in a pneumothorax (air in the pleural space which prevents full re-expansion of the lung within the pleural space). If sutures are used to close the incision after chest tube removal, it is possible to entrap harmful microbes, which could result in more extensive infection. In addition, when the tube is removed from the incision, healthcare professionals can be exposed to the tube and fluid from within the patient, which can also result in infection or exposure to harmful microbes. While most healthcare practitioners practice universal fluid precautions and try to avoid contamination with bodily fluids, removal of the tube can frequently result in dispersion of fluid from the incision and/or tube that can contaminate the area around the patient as well as the person removing the tube.

In particular, the global COVID-19 pandemic has emphasized the need to minimize environmental contamination with macroscopic as well as microscopic secretions as well as aerosolization of microbes, which could be lethal to those residing in the healthcare environment (i.e., healthcare workers and other patients) (see, e.g., Cha, {2020}, 'CDC Says More Than 9,000 Healthcare Workers Had Tested Positive For Coronavirus As Of April 9', *Washington Post*, Apr. 14, 2020; and Stobbe, {2020} 'Health Care Workers are 10%-20% of US Coronavirus Cases'; *Associated Press (AP) News*, Apr. 14, 2020). While COVID-19 has affected the globe in 2020, a new and augmented approach to disease prevention will be sought in the future.

Based on the foregoing, a solution that seals the incision is desirable. Additionally, a solution that provides protection for medical professionals during and after removal of the tube is desirable.

SUMMARY

In one aspect, a medical device for use with an associated tube inserted into an incision formed in skin or tissue of a patient includes a dressing including an opening sized to receive and allow movement of the associated tube. A valve is operatively connected with the opening of the dressing and includes a main body; and an opening formed in a portion of the main body. The opening is sized and dimensioned to accommodate the surgical tube.

In another aspect, a medical device for use with an associated tube inserted into an incision formed in skin or tissue of a patient includes a dressing with an opening. A sheath is detachably secured to a portion of the dressing and surrounds the opening. A valve is operatively connected with the opening of the dressing and includes a main body; an opening formed in a portion of the main body and sized to receive and allow movement of the associated tube; and a flap connected to a portion of the main body and sized to cover the opening. When the associated tube is removed from the incision, the sheath is configured to surround the associated tube and detach from the dressing.

In yet another aspect, a method of using a medical device with an associated surgical tube inserted into an incision formed in skin or tissue of a patient includes using a medical device comprising: a dressing including an opening; a sheath detachably secured to a portion of the dressing and surrounding the opening; and a valve operatively connected with the opening of the dressing that includes: a main body and an opening formed in a portion of the main body and sized to receive and allow movement of the associated tube. The method includes: inserting the associated tube through the opening of the valve; sliding the medical device along a length of the associated tube; attaching the dressing to a portion of a patient to enclose the incision; removing the associated tube from the incision; and removing the sheath from the dressing after the associated tube is contained therein.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

DESCRIPTION OF THE DRAWINGS

The present invention exists in the construction, arrangement, and combination of the various parts of the device, and steps of the method, whereby the objects contemplated are attained as hereinafter more fully set forth, specifically pointed out in the claims, and illustrated in the accompanying drawings in which:

FIGS. 3A-D are schematic views of a valve of the medical device of FIG. 1;

DETAILED DESCRIPTION

Various embodiments of a medical device and associated methods of using the medical device for use with a surgical tube in conjunction with a surgical procedure are disclosed herein. Generally, the medical device includes a dressing to enclose an incision made during surgery for insertion of the surgical tube, a valve installed on a portion of the dressing to receive the surgical tube and help seal the incision after removal of the surgical tube, and a sheath attached to the dressing that covers the surgical tube after removal from the pleural chest cavity of the patient. In certain embodiments, the valve is sized and dimensioned to receive the tube, and includes a flap to seal the valve, and thus seal the incision, after removal of the surgical tube. In other embodiments, the sheath can be detachable from the dressing to enclose the surgical tube after removal from the patient to prevent exposure of the tube to medical professionals and the ambient environment.

Figure 1:
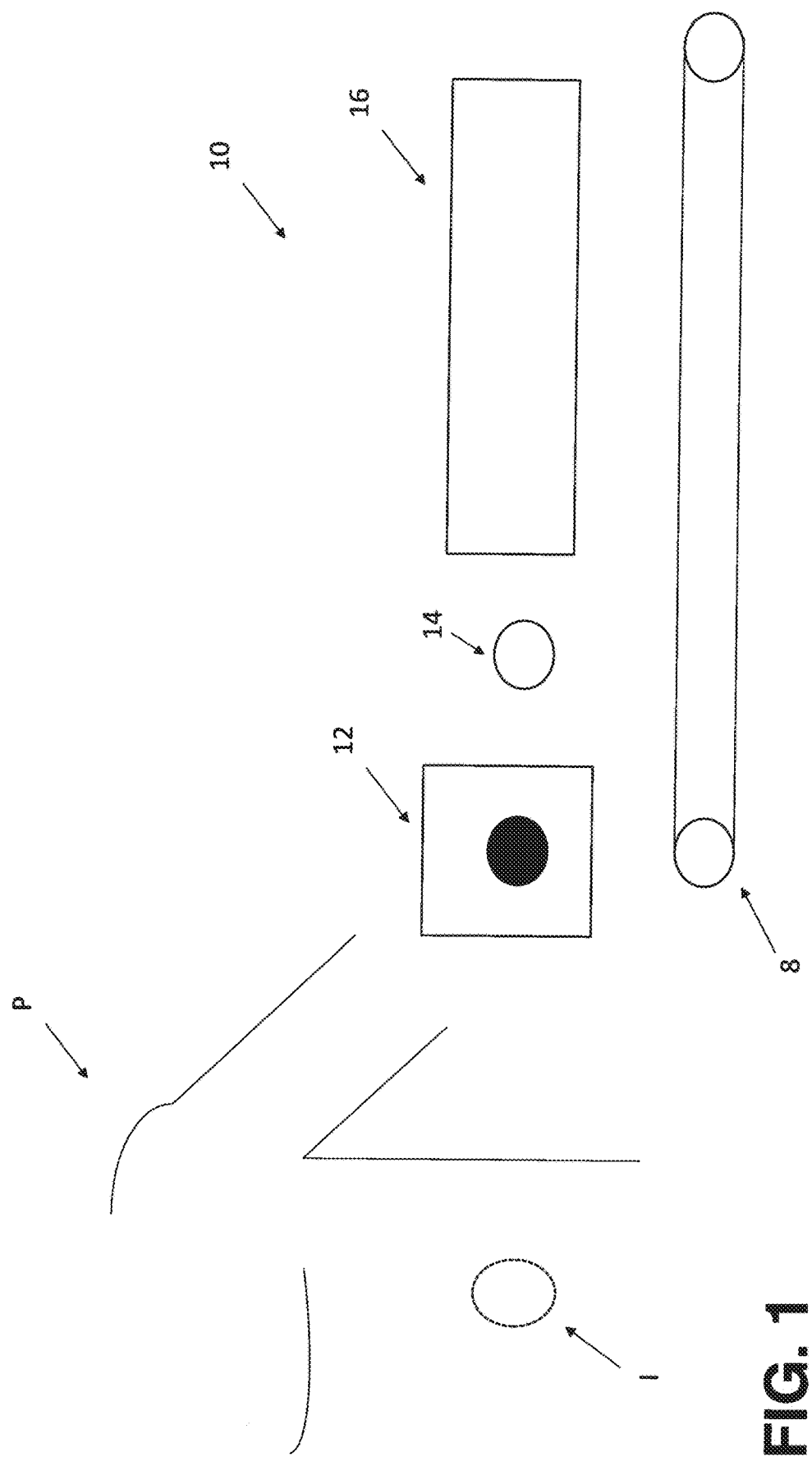
FIG. 1 is an exploded view of an exemplary embodiment of a medical device.

Referring now to the drawings wherein the showings are for purposes of illustrating the exemplary embodiments only and not for purposes of limiting the claimed subject matter, FIG. 1 depicts an exemplary embodiment of a medical device 10 for use with an associated surgical tube 8. The surgical tube 8 is used during surgery, in which the surgical tube 8 is inserted into an incision I formed in a pleural chest cavity of a patient P to drain fluid from the pleural chest cavity. For example, the surgical tube 8 can comprise a chest tube, which is used to drain the pleural cavity space following lung surgery. By leaving a chest tube in place after an operation, fluid and/or air is evacuated from the pleural space, while providing suction to help keep the lung fully expanded. Chest tubes are sometimes placed primarily into the thoracic cavity to drain fluid and/or air in cases of pneumothorax or hydrothorax.

Other surgical tubes that require sanitary removal to prevent contamination of the field/environment as well as aerosolization of patient secretions include vascular cannulas used for extracorporeal membrane oxygenation (ECMO), central venous access lines, nasogastric tubes, endotracheal tubes, percutaneous endoscopic gastrostomy tubes (PEG), as well as various types of enteric feeding tubes. Additionally, drainage systems (such as a Jackson-Pratt (JP) wound drain or other wound drains) would additionally benefit from an improved system in which the insertion site is controlled with an appropriate dressing system while containing the patient's excretions within a closed system to prevent contamination of the patient, the healthcare worker removing the in-dwelling tube or drainage device, or subsequent healthcare workers who enter the room and come into contact with bed rails, linens, the floor, ceiling, and walls that could have been contaminated during standard/traditional tube removal.

As shown in FIG. 1, the device 10 includes a dressing 12 configured to cover and seal the incision I, a valve 14 attached to a portion of the dressing 12 and also configured to seal the incision I, and a sheath 16 attached to a portion of the dressing 12 and sized to cover, enclose, or otherwise surround the surgical tube 8 during removal from the incision I. Each of the dressing 12, the valve 14, and the sheath 16 are described in more detail below.

Figure 2:
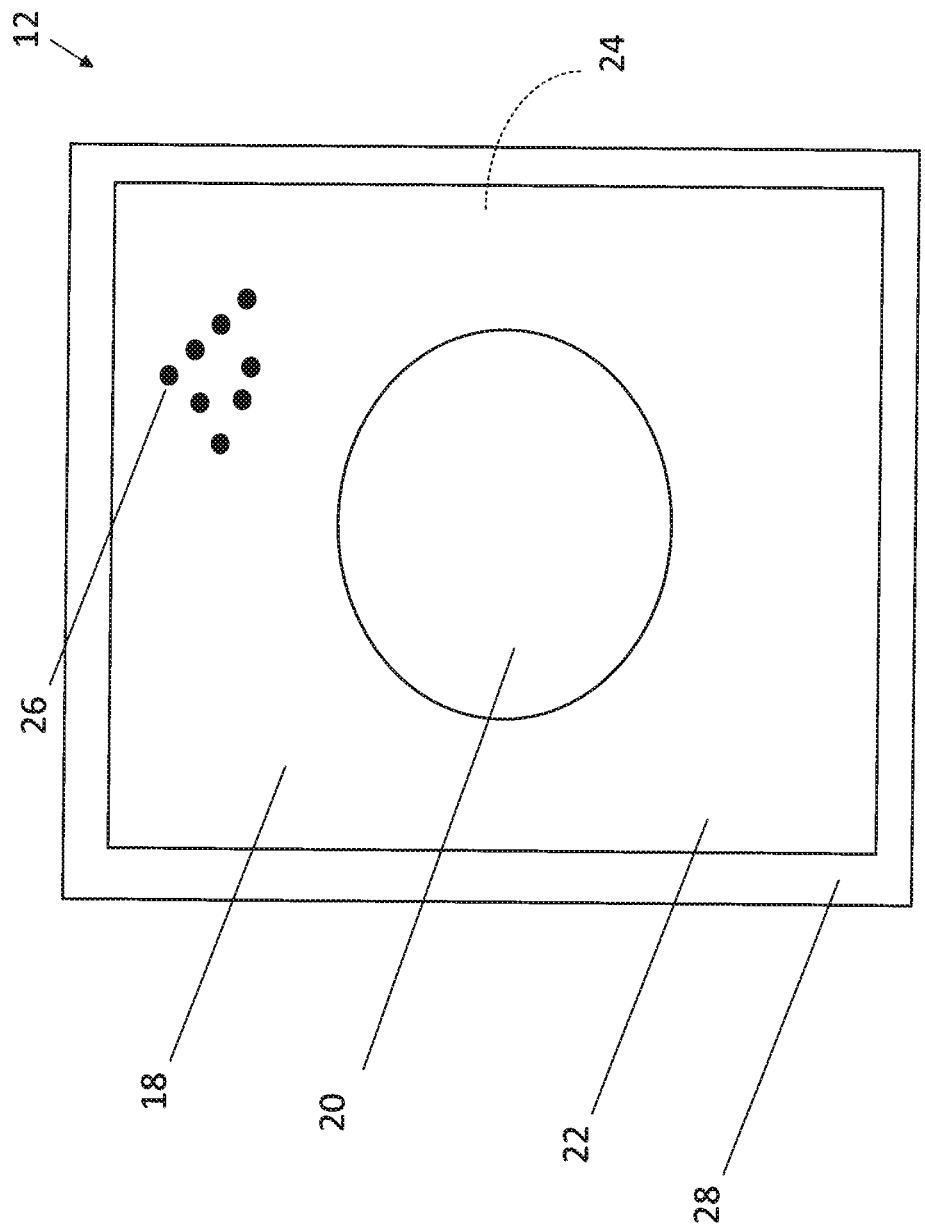
FIG. 2 is a schematic view of a dressing of the medical device of FIG. 1.

FIG. 2 shows an example of the dressing 12. The dressing 12 can include a main dressing body 18 with a dressing opening 20 through which the valve 14 can be installed. The dressing 12 can include a cover side 22 (i.e., a "back" side) which covers the incision I, and an opposing exposed side 24 (i.e., a "front side") which is exposed to the ambient environment. The cover side 22 can include an adhesive 26 (depicted in FIG. 2 as small dark circles) configured to attach (i.e., stick) to the patient P to address the dressing 12 thereto. As shown in FIG. 2, the adhesive 26 is only shown on a portion of the cover side 22 for illustrative purposes; however, it will be appreciated that the adhesive 26 can cover substantially the entirety of the cover side 22. A cover (not shown) can be overlaid onto the cover side 22 to cover the adhesive 26, thereby preventing anything (e.g., dust, debris, microbes, and so forth) from sticking to the adhesive 26 until it is ready for placement over the incision I. A rim 28 of the dressing 12 provides an airtight seal around the incision I when the dressing 12 is attached to the patient P via the adhesive 26. The dressing 12 can be made of a substantially pliable material (e.g., plastic). That is, the dressing 12 is pliable enough to be manipulated, but rigid enough to avoid tearing. As shown in FIG. 2, the dressing 12 has a rectangular shape; although any planar shape can be suitable. The dressing 12 can be any suitable dressing, including commercially-available dressings (such as, for example, a dressing manufactured by Hollister, Inc. Libertyville, Ill., USA).

FIGS. 3A-D show examples of the valve 14. Starting at FIG. 3A, the valve 14 includes a main valve body 30 with a valve opening 32. The valve opening 32 is sized and dimensioned to receive and accommodate the surgical tube 8 (FIG. 1). Typically, surgical tubes used in pleural chest cavity operations can have a diameter ranging from approximately 5 mm to approximately 12 mm. Thus, a diameter of the valve opening 32 can have similar dimensions as the diameter of the surgical tube 8 to receive and accommodate the surgical tube 8. In some examples, the valve 14 can include an adapter (not shown) to allow the valve 14 to fit any-sized surgical tube 8. In some embodiments, the valve 14 is configured to accommodate a range of sizes of surgical tubes 8. For example, the valve opening 32 of the valve 14 can accommodate small-sized tubes (e.g., IV lines, and so forth); medium-sized tubes (e.g., chest tubes), or larger-sized tubes (e.g., extracorporeal membrane oxygenation (ECMO) cannulas).

In an alternate embodiment, as shown in FIG. 3B, the valve 14 can include a knock-out portion or element 34 centrally located on the main valve body 30. In lieu of providing a predefined opening 32, the knock-out portion 34 can be made of a substantially thin, flexible material (e.g., a thin, mesh-like material). When the medical device 10 is fitted on the surgical tube 8, an end of the surgical tube 8 can perforate (i.e., knock out) a portion of the knock-out portion 34 to create the valve opening 32. The knock-out portion 34 allows the valve opening 32 to be formed with substantially the exact size of the diameter of the surgical tube 8, which can prevent fluid or microbes from entering or exiting the patient P during the surgical procedure through the valve opening 32. Alternatively, the knock-out portion 34 can include a series of perforated portions (not shown) corresponding to the potential sizes of the surgical tube 8. That is, a first perforated portion can be sized to 5 mm, a second perforated portion can be sized to 6 mm, and so forth. The end of the surgical tube 8 can punch-out the corresponding perforated portion upon installation of the medical device 10 onto the surgical tube 8.

As shown in FIG. 3C, the valve 14 can also include a flap 36 that is sized and dimensioned to cover the valve opening 32. The flap 36 is disposed on the side of the main valve body 30 that faces the patient P. The flap 36 covers the valve opening 32 after removal of the surgical tube 8 to provide a seal around the incision I, as shown in FIG. 3D. The flap 36 can have any suitable dimensions to cover the valve opening 32 (e.g., approximately 6 mm to approximately 13 mm to cover any size of the valve opening ranging from approximately 5 mm to approximately 12 mm).

The flap 36 can be attached to the main valve body 30 with a hinged connection or joint 38, so that the flap 36 is resiliently biased relative to the main valve body 30. The hinged connection 38 allows the flap 36 to be pushed away from the valve opening 32 when the surgical tube 8 is inserted through the valve opening 32 (i.e., an open state). As shown in FIG. 3C, the flap 36 can be biased upwards relative to the valve main body 30 by the surgical tube 8 when the surgical tube 8 is inserted through the valve opening 32. As shown in FIG. 3D, upon removal of the surgical tube 8 (not shown in FIG. 3D), the flap 36 is no longer biased upward, and can move towards a natural collapsed state covering the valve opening 32 (i.e., a closed state).

As shown in FIGS. 3A-D, the valve 14 has a circular shape, although any planar shape can be suitable. The valve 14 can be made of a substantially rigid material (e.g., plastic). That is, the valve 14 is flexible enough to be manipulated, but rigid enough to avoid tearing and to allow movement of the surgical tube 8 therethrough. The valve 14 can be any suitable valve, including commercially-available valves. In addition, although the device 10 is described herein as including only one valve 14, the device 10 can include any suitable number of valves 14 (e.g., two or more).

Figure 4:
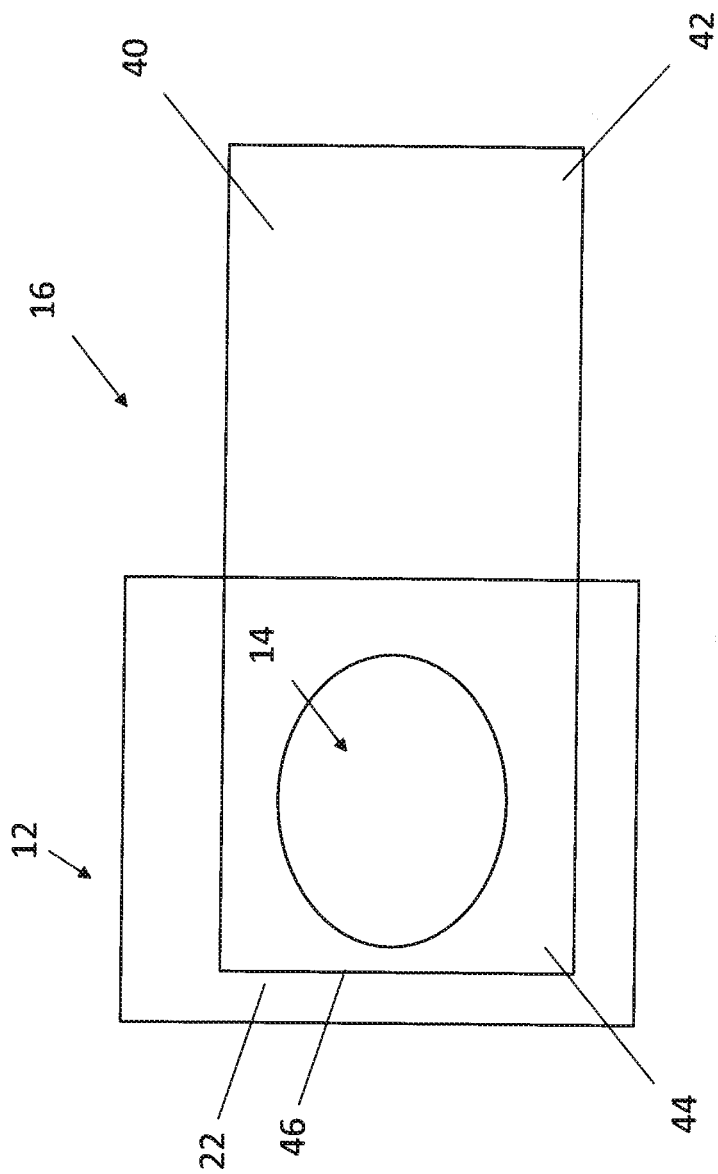
FIG. 4 is a schematic view of a sheath of the medical device of FIG. 1.

FIG. 4 shows an example of the sheath 16. As shown in FIG. 4, the sheath 16 includes a main sheath body 40 is attached to the exposed side 24 of the dressing 12 to surround the valve 14. The sheath 16 surrounds the surgical tube 8 (not shown in FIG. 4) when the medical device 10 is installed on the surgical tube 8. As described in more detail below, the sheath 16 has a closed end 42, and open end 44, and the open end 44 is attached to the dressing 12. The sheath 16 has a length and width to completely cover the surgical tube 8 so that medical professionals are not exposed to the surgical tube 8 upon removal from the incision I.

The main sheath body 40 can be attached to the exposed side 24 of the dressing 12 with an attachment interface 46. In some examples, the attachment interface 46 can include a perforated portion (or any other suitable attachment mechanism, such as snaps, buttons, hook-and-loops, and so forth), so that the sheath 16 (and the surgical tube 8 contained therein) can easily be removed from the dressing 12 when the surgical tube 8 is removed from the incision I.

The sheath 16 can be made of a substantially pliable rigid material (e.g., plastic). That is, the sheath 16 is pliable enough to be manipulated, rigid enough to avoid tearing, and impermeable to air or fluid that can enter the surgical environment of the surgical tube 8. In addition, the sheath 16 can be made of a transparent material to allow a medical professional to see the surgical tube 8 within the sheath 16. As shown in FIG. 4, the sheath 16 has a tubular shape; although any 3-dimensional shape can be suitable. The sheath 16 can be any suitable sheath, including commercially-available sheaths.

Figure 5:
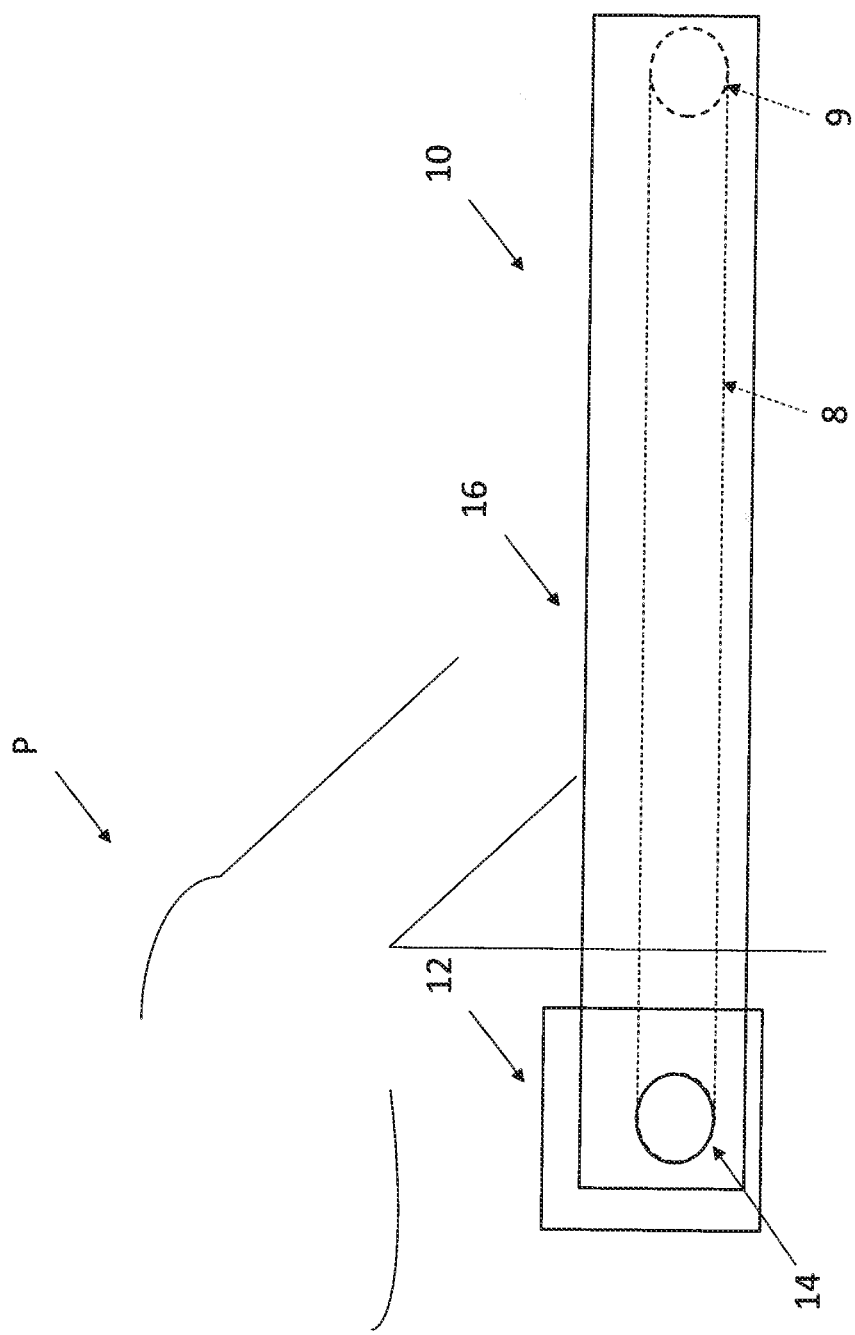
FIG. 5 is an assembled view of an exemplary embodiment of the medical device of FIG. 1.

FIG. 5 shows an assembled view of the medical device 10. As noted, the surgical tube 8 is installed into the incision I (not shown in FIG. 5) into the pleural chest cavity of the patient P. A drain end 9 of the surgical tube 8, that is opposite from the end of the surgical tube 8 that is inside the pleural chest cavity of the patient P, is removed from the waste receptacle (not shown) and capped or pinched. The medical device 10 is then fit onto to the surgical tube 8 so that the surgical tube 8 (i) is inserted through the valve 14 and (ii) is surrounded by the sheath 16. The dressing 12 is positioned over the surgical incision I to enclose the incision I (and thus enclose the portion of the surgical tube 8 in the pleural chest cavity), and the sheath 16 covers the remainder of the surgical tube 8.

Figure 6:
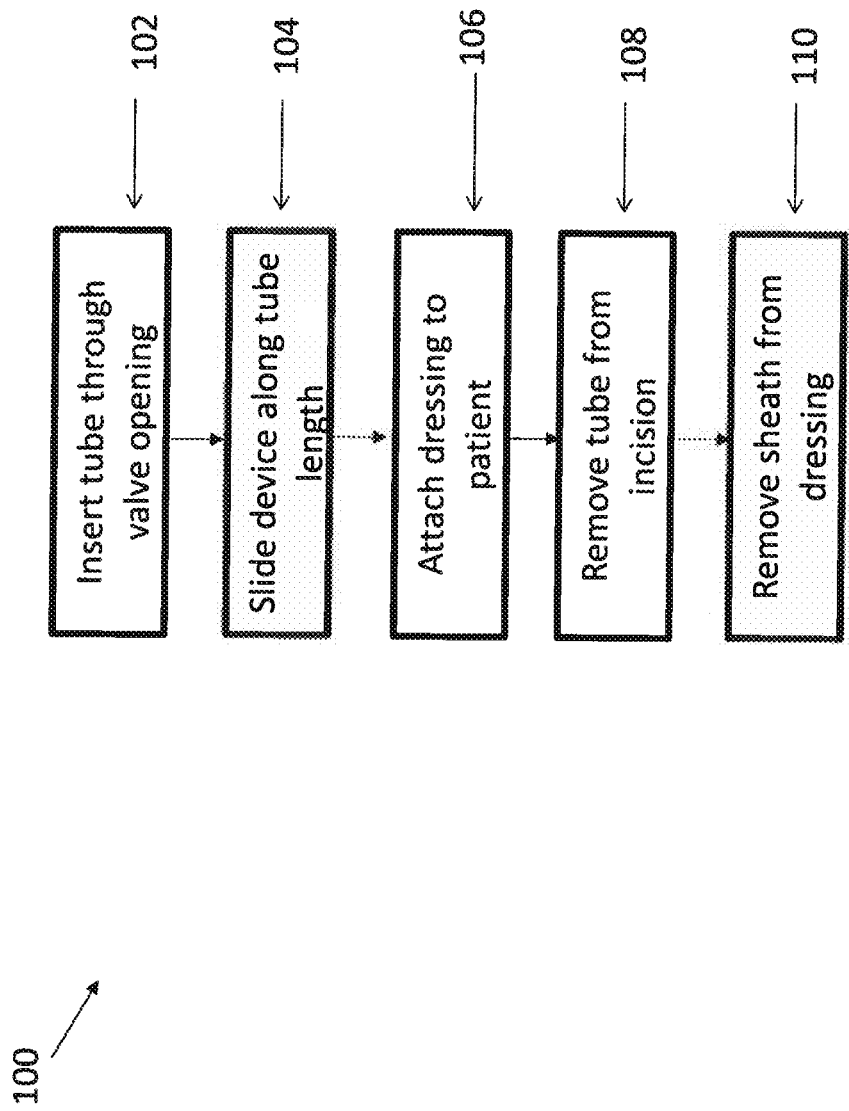
FIG. 6 is a flow chart of an exemplary embodiment of a process for using the medical device of FIG. 1.

FIG. 6 shows a flow chart of a method or process 100 of using the medical device 10. Before the method 100 commences, the surgical tube 8 is already inserted into the pleural chest cavity of the patient P via the incision I. In some embodiments, before the method 100 commences, the valve 14 can be installed within the dressing opening 20 of the dressing 12.

At an operation 102 of the method 100, a drain end 9 of the surgical tube 8, opposite the end in the pleural chest cavity of the patient P, is inserted through the valve opening 32 (or alternatively through the knock-out portion 34 in appropriate embodiments). The flap 36 can be biased by the surgical tube 8 to expose (i.e., not cover) the valve opening 32. In another example, the flap 36 can be held open by an instrument (not shown) while the surgical tube 8 is inserted in the valve opening 32.

At an operation 104 of the method 100, the medical device 10 is slid along a length of the surgical tube 8. To do so, a medical professional can grasp the dressing 12 by hand and move or otherwise manipulate the dressing 12 along the length of the surgical tube 8. The medical device 10 is slid along the length of the tube until the dressing 12 is adjacent the incision I. Once the dressing 12 reaches the patient P, it will be appreciated that the exposed portion of the surgical tube 8 (i.e., the portion of the surgical tube 8 that is not inside the patient P) is surrounded in its entirety by the sheath 16, and extends from the incision I through the valve opening 32 of the valve 14.

At an operation 106 of the method 100, the dressing 12 is attached to the patient P. To do so, the medical professional presses the dressing 12 so that the adhesives 26 adheres to skin of the patient P. When included, the cover can be removed from the cover side 22 of the dressing 12 in appropriate embodiments.

At an operation 108 of the method 100, the surgical tube 8 is removed from the incision I. To do so, the medical professional can grasp the sheath 16 and grasp the surgical tube 8 and manually pull the surgical tube 8 out of the patient and into the sheath 16. The surgical tube 8 is pulled until an end of the surgical tube 8 that was within the pleural chest cavity of the patient P is visible inside of the sheath 16. Once that end of the surgical tube 8 is removed from the patient P and is within the sheath 16, the flap 36 of the valve 14 is no longer biased open by the surgical tube 8. The flap 36 moves to cover the valve opening 32, sealing the incision I from the ambient environment and preventing fluid or microbes from entering or exiting from the seal provided by the valve 14 and the dressing 12. Thus, the incision I is sealed from the ambient environment. The incision I can then be sutured.

At an operation 110 of the method 100, the sheath 16 is removed from the dressing 12. To do so, the attachment interface 46 of the sheath 16 is removed from the exposed side 24 of the dressing 12 (e.g., by severing the perforations in the attachment interface from the main dressing body 18). As noted, the surgical tube 8 is enclosed within the main sheath body 40 at this point. Once removed, the sheath 16, with the surgical tube 8 completely enclosed therein, can be safely discarded, while the dressing 12 remains affixed to the patient P. In this manner, the medical professionals are not exposed to the surgical tube 8 or fluid or microbes from the patient P. In an alternative embodiment, the sheath 16 can be attached to the dressing 12 after the dressing 12 is affixed to the patient P. The sheath 16 is positioned to surround the surgical tube 8, and then the sheath 16 is removed from the dressing 12. The surgical tube 8 and the sheath 16 can then be discarded without exposing the patient P or any present medical professional to microbes present on the surgical tube 8 after removal from the patient P.

Figure 7:
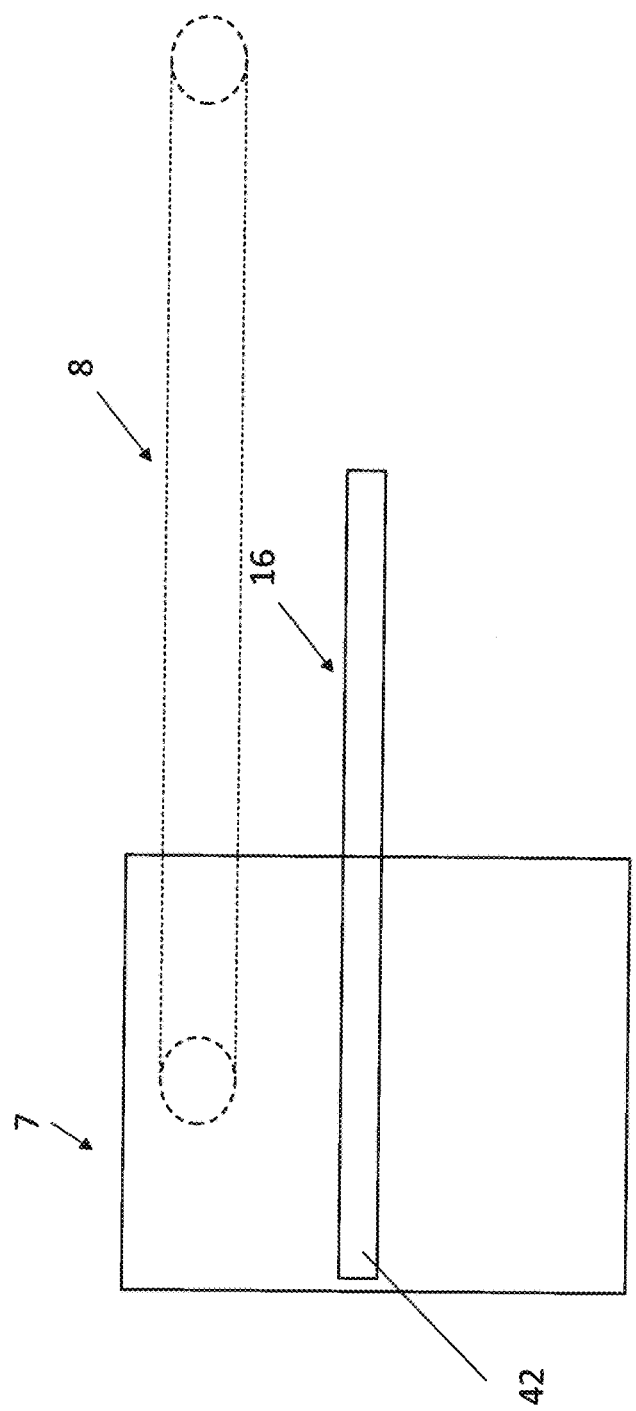
FIG. 7 is an assembled view of a portion of the medical device of FIG. 1.
Figure 8:
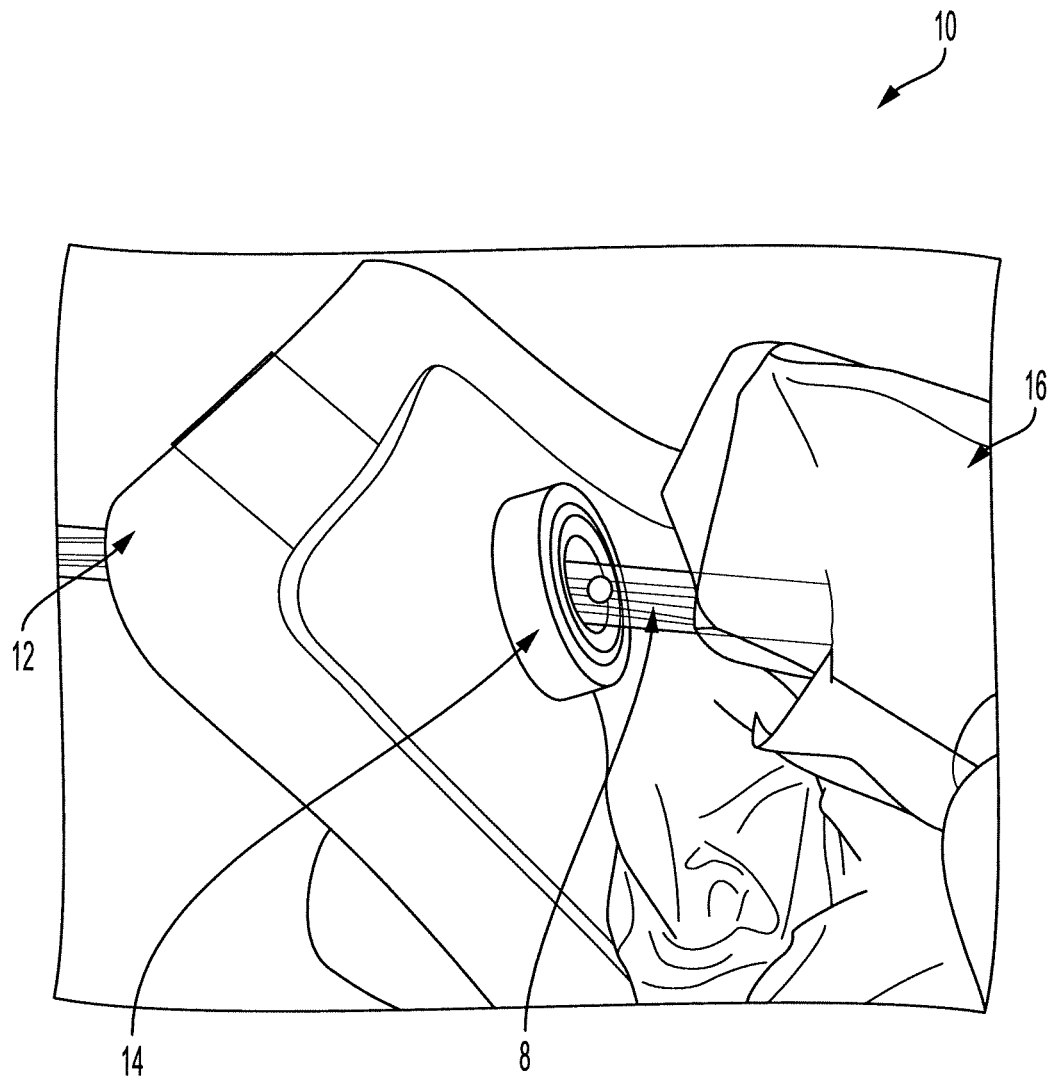
FIGS. 8-14 are alternative views of the medical device of FIG. 1.
Figure 9:
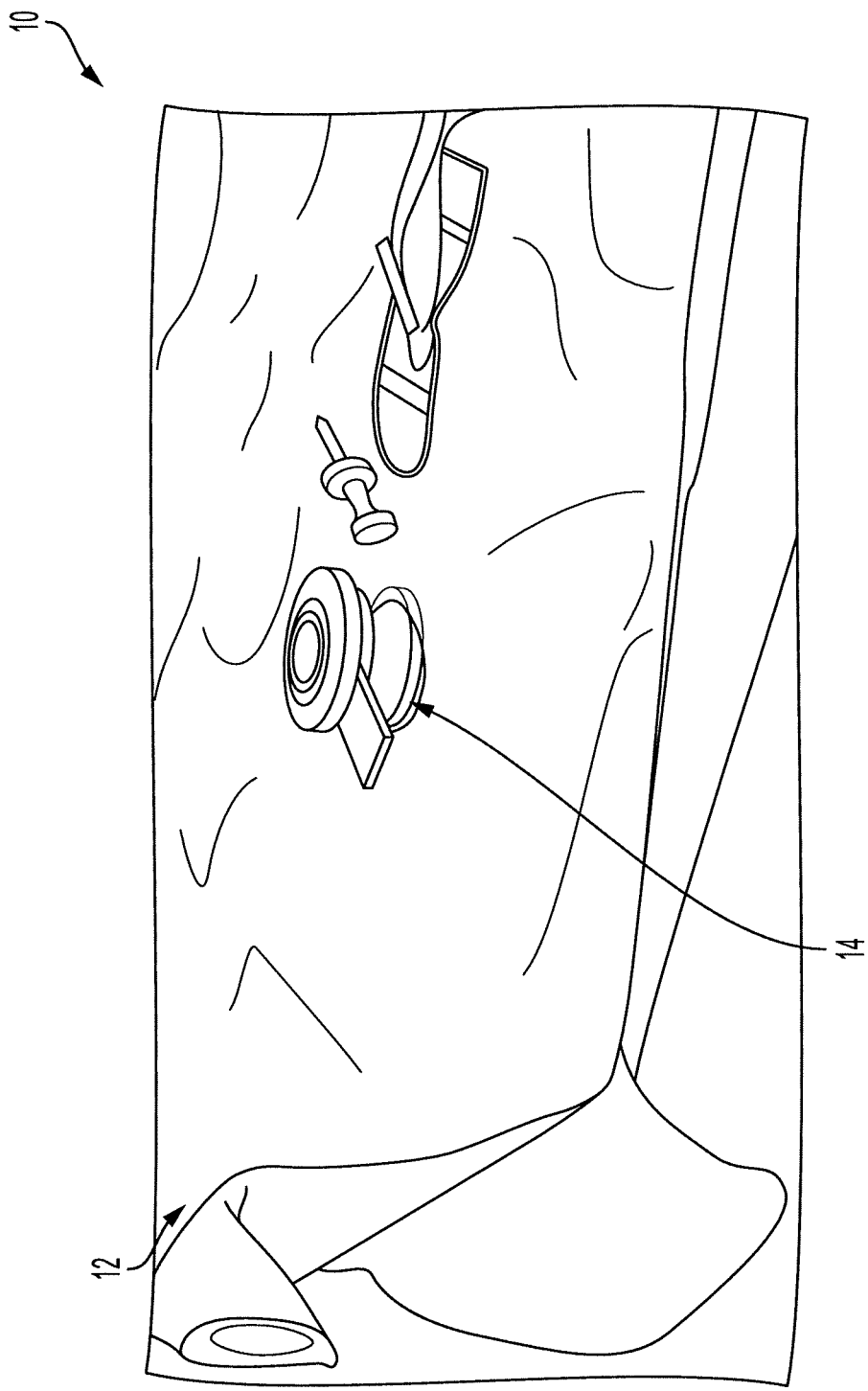
Figure 10:
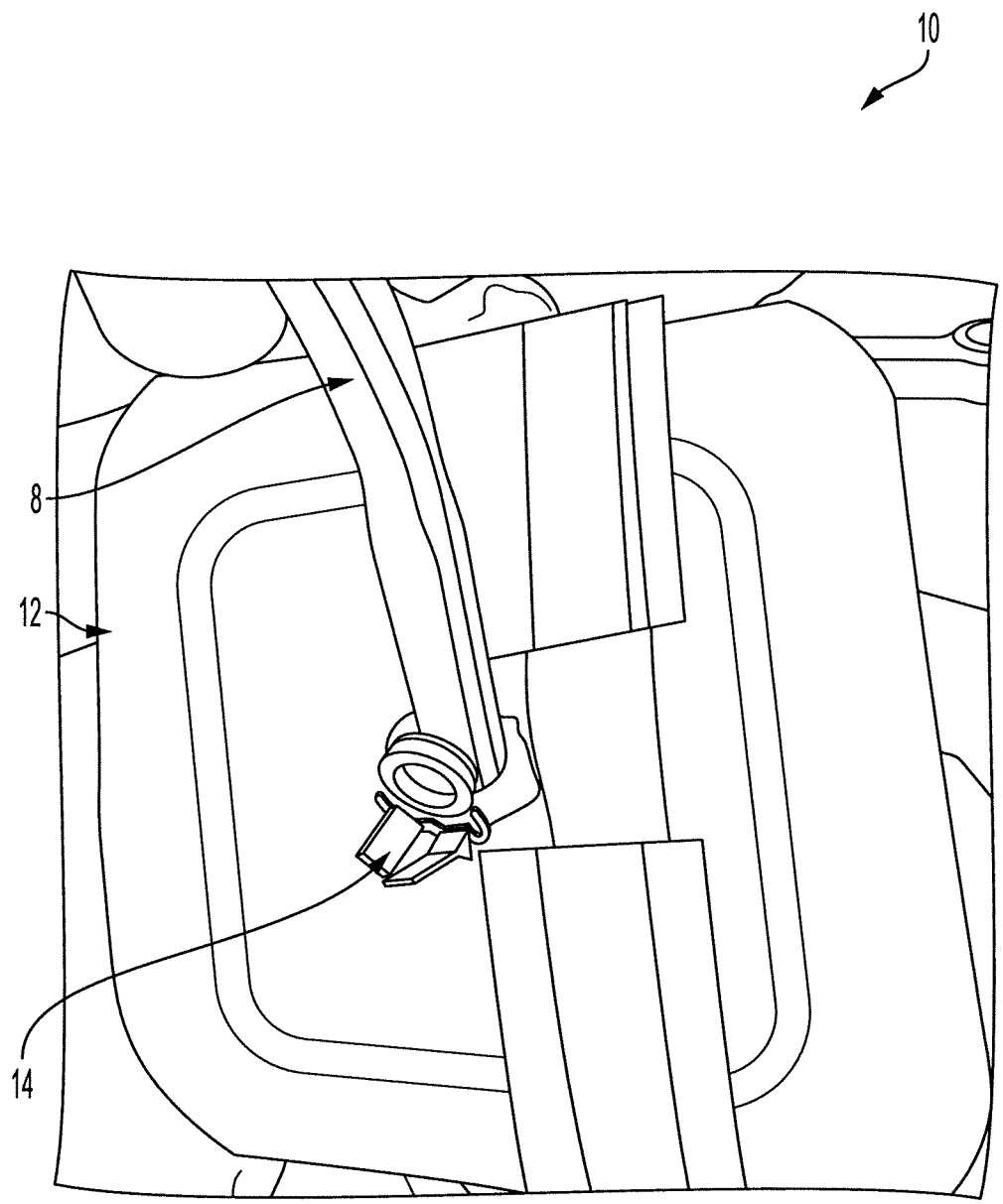
Figure 11:
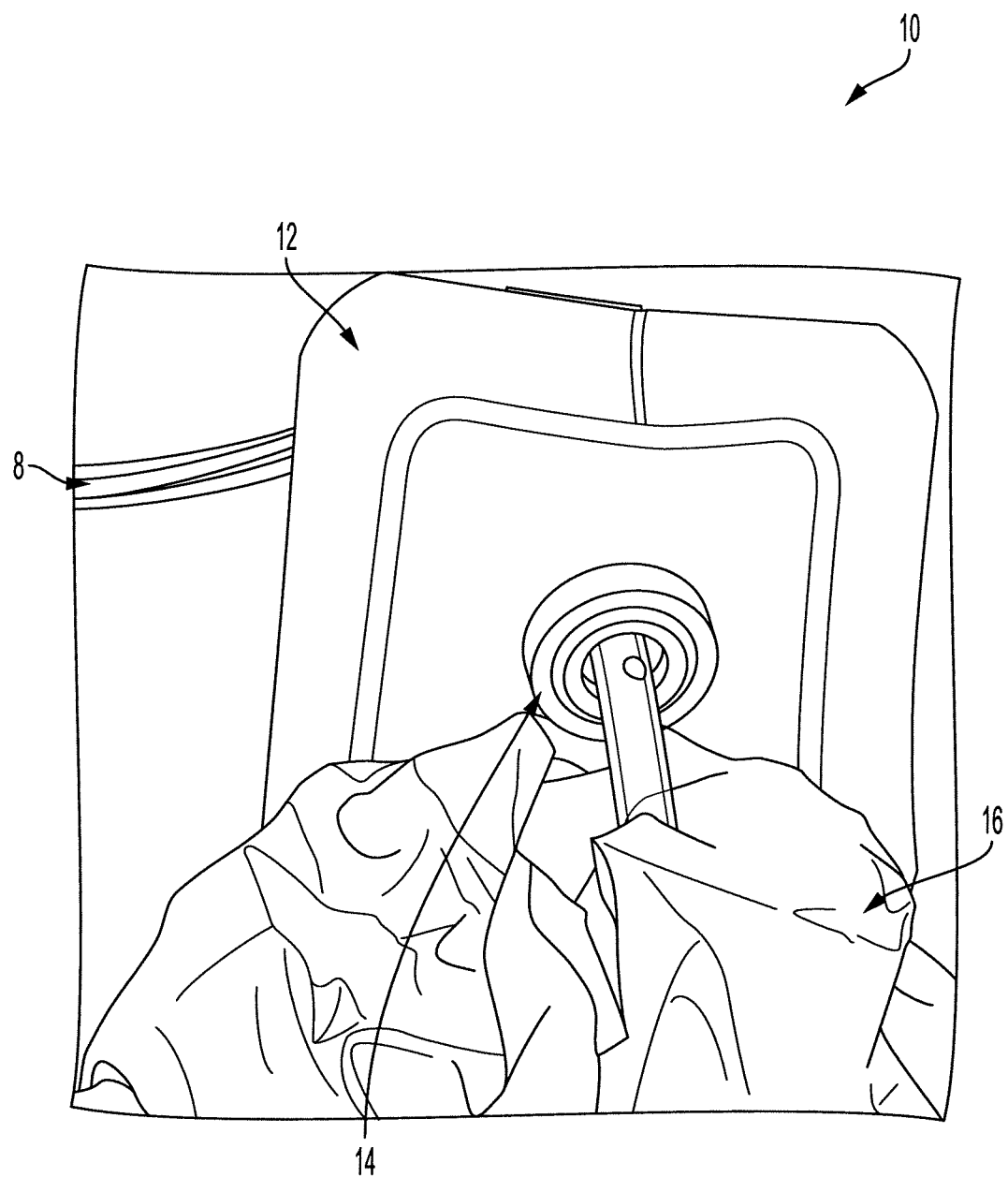
Figure 12:
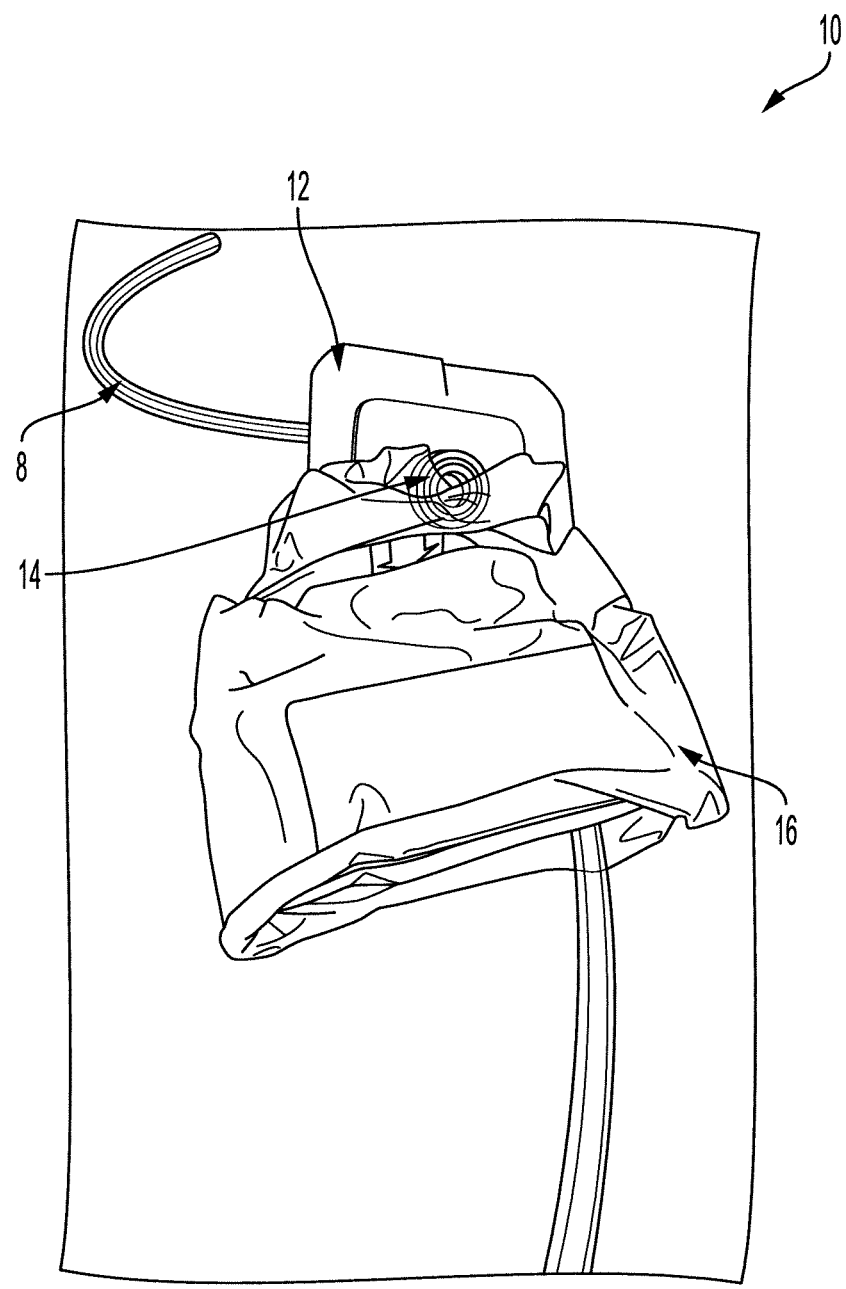
Figure 13:
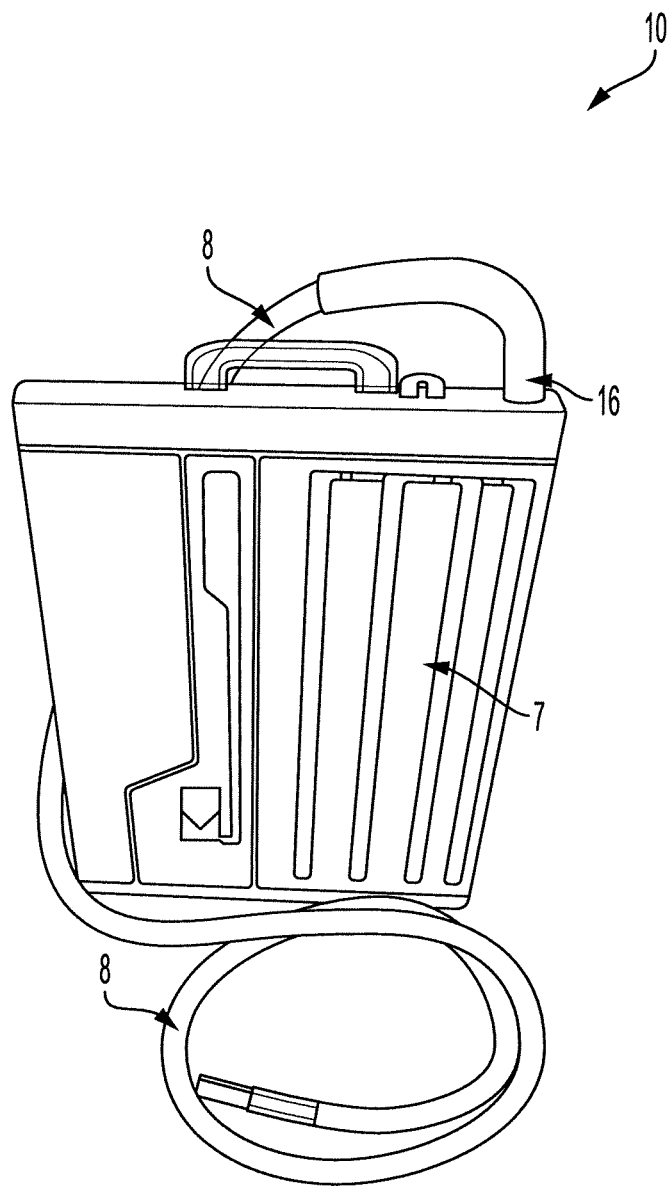
Figure 14:
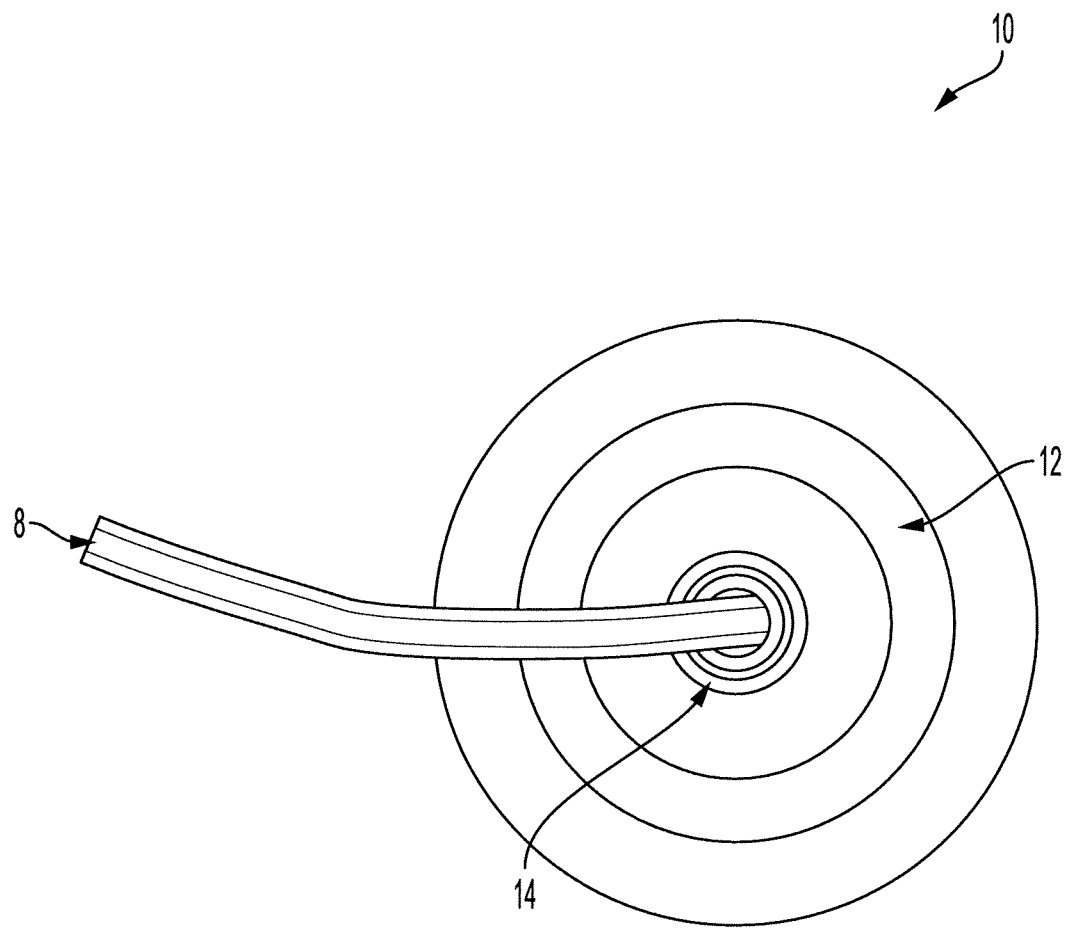

In a further embodiment, shown in FIG. 7, the open end 42 of the sheath 16 disposed away from the patient P is attached or secured to a collection box 7 configured to collect fluid from the pleural chest cavity of the patient P. The collection box 7 can be any suitable collection box, including commercially-available collection box (such as, for example, a Pleur-Evac® drainage system, available from Teleflex®, Morrisville, N.C., USA). In this embodiment, the sheath 16 can be mounted over the surgical tube 8, but can retracted and hygienically packaged near the collection box 7. That is, the sheath 16 can be stored adjacent the surgical tube 8 on the collection box 7 in a "rolled-up" configuration. When the surgical tube 8 is ready for removal, the sheath 16 could be unpackaged (i.e., unwrapped or unrolled) and advanced onto the dressing 12 until the attachment interface 46 is attached to the dressing 12 for removal of the surgical tube 8. After removal of the surgical tube 8, the sheath 16 and the surgical tube 8 are discarded, and dressing 12 remains attached to the patient P.

FIGS. 8-14 show different views of the medical device 10.

The above description merely provides a disclosure of particular embodiments of the invention and is not intended for the purposes of limiting the same thereto. As such, the invention is not limited to only the above-described embodiments. Rather, it is recognized that one skilled in the art could conceive alternative embodiments that fall within the scope of the invention.

The invention claimed is:

1. A medical device for use with an associated tube inserted into an incision formed in skin or tissue of a patient, the medical device comprising:
 a dressing including an opening sized to receive and allow movement of the associated tube;
 a sheath secured to a portion of the dressing and surrounding the dressing opening; and
 a valve operatively connected with the opening of the dressing, the valve including:
  a main body;
  a valve opening formed in a portion of the main body, the opening being sized and dimensioned to accommodate the associated tube; and
  a flap connected to a portion of the main body and sized to cover the valve opening;
 wherein, when the associated tube is removed from the incision, the sheath is configured to surround the associated tube and detach from the dressing.

2. The medical device of claim 1, wherein:
 when the associated tube is disposed in the opening of the dressing, the valve is in an open state in which the flap portion does not cover the opening, and
 when the associated tube is not disposed in the opening of the dressing, the valve is in a closed state in which the flap portion covers the opening.

3. The medical device of claim 1, wherein the valve opening has a diameter of approximately 5 mm to approximately 12 mm.

4. The medical device of claim 1, wherein the valve opening comprises a knockout element configured to perforate when the associated tube is inserted to form the valve opening.

5. The medical device of claim 1, wherein the dressing includes a front side and a back side, the back side including:
 an adhesive disposed thereon and configured for attachment to the patient.

6. The medical device of claim 5, wherein the dressing and the valve are configured to form a fluid-tight seal about the incision when:
 the dressing is secured to the patient via the adhesive; and
 the valve is in the closed state when the associated tube is removed from the incision and the opening in the dressing.

7. The medical device of claim 1, wherein the sheath includes a detachment interface configured for detachment from the dressing when the associated tube is removed from the incision.

8. The medical device of claim 1, wherein the sheath is configured to completely surround the associated tube and form a seal around an end of the associated tube that was inserted into the patient through the incision when the associated tube is removed from the incision.

9. A medical device for use with an associated tube inserted into an incision formed in skin or tissue of a patient, the medical device comprising:
 a dressing including an opening;
 a sheath detachably secured to a portion of the dressing and surrounding the opening; and
 a valve operatively connected with the opening of the dressing, the valve including:
  a main body;
  a valve opening formed in a portion of the main body and sized to receive and allow movement of the associated tube; and
  a flap connected to a portion of the main body and sized to cover the valve opening;
 wherein, when the associated tube is removed from the incision, the sheath is configured to surround the associated tube and detach from the dressing.

10. The medical device of claim 9, wherein:
 when the associated tube is disposed in the valve opening, the flap is in an open state in which the flap does not cover the valve opening,
 when the associated tube is not disposed in the valve opening, the flap is in a closed state in which the flap covers the valve opening.

11. The medical device of claim 9, wherein the opening has a diameter of approximately 5 mm to approximately 12 mm.

12. The medical device of claim 9, wherein the opening comprises a knockout element configured to perforate when the associated tube is inserted to form the opening.

13. The medical device of claim 9, wherein the dressing includes a front side and a back side, the back side including:
 an adhesive disposed thereon and configured for attachment to the patient.

14. The medical device of claim 13, wherein the dressing and the valve are configured to form a fluid-tight seal about the incision when:
 the dressing is secured to the patient via the adhesive; and the valve is in a closed state in which the flap covers the opening in the valve when the associated tube is removed from the incision and the opening in the valve.

15. The medical device of claim 9, wherein the sheath includes a detachment interface configured for detachment from the dressing when the associated tube is removed from the incision.

16. The medical device of claim 15, wherein the sheath is configured to surround the associated tube and form a seal around an end of the associated tube that was inserted into the patient through the incision when the associated tube is removed from the incision.

17. A method of using a medical device with an associated surgical tube inserted into an incision formed in skin or tissue of a patient, the medical device comprising: a dressing including an opening; a sheath detachably secured to a portion of the dressing and surrounding the opening; and a valve operatively connected with the opening of the dressing, the valve including: a main body and a valve opening formed in a portion of the main body and sized to receive and allow movement of the associated tube; the method including:
  inserting the associated tube through the valve opening;
  sliding the medical device along a length of the associated tube;
  attaching the dressing to a portion of a patient to enclose the incision;
  removing the associated tube from the incision; and
  removing the sheath from the dressing after the entire associated tube is contained therein.

18. The method of claim 17, wherein the valve further includes a flap connected to a portion of the main body and sized to cover the valve opening, and the method further includes:
  forming a fluid-tight seal about the incision when:
    the dressing is attached to the patient; and
    the valve is in a closed state in which the flap covers the valve opening
  when the associated tube is removed from the incision and the valve opening.

19. The method of claim 17, wherein the sheath includes a detachment interface configured for detachment from the dressing when the associated tube is removed from the incision, and the method further includes:
  detaching the detachment interface of the sheath from the dressing, wherein the sheath is configured to surround the associated tube and form a seal around an end of the associated tube that was inserted into the patient through the incision when the associated tube is removed from the incision.

\* \* \* \* \*